United States Patent [19]

Ehrhardt et al.

[11] Patent Number: 5,419,955
[45] Date of Patent: May 30, 1995

[54] METHOD FOR IMMOBILIZING SUPERABSORBENT POLYMER AND PRODUCTS DERIVED THEREFROM

[75] Inventors: Kenneth C. Ehrhardt, Charlotte; John B. Hopkins, Jr., Pineville; Joanne C. Maheras, Charlotte; David R. McWilliams, Davidson, all of N.C.

[73] Assignee: Hoechst Celanese Corporation, Somerville, N.J.

[21] Appl. No.: 79,694

[22] Filed: Jun. 17, 1993

Related U.S. Application Data

[63] Continuation of Ser. No. 805,538, Dec. 11, 1991, abandoned.

[51] Int. Cl.6 .............. A61L 15/22; A61L 15/24; A61L 15/28
[52] U.S. Cl. ...................... 428/283; 264/28; 264/207; 428/290
[58] Field of Search .............. 523/105; 428/283, 290; 264/204, 207

[56] References Cited

U.S. PATENT DOCUMENTS

| | | | |
|---|---|---|---|
| 2,362,182 | 11/1942 | Baker . | |
| 3,664,103 | 6/1972 | Harper et al. | 128/156 |
| 4,076,663 | 2/1978 | Masuda et al. | 525/54.31 |
| 4,105,033 | 8/1978 | Chatterjee et al. . | |
| 4,115,332 | 9/1978 | Young et al. | 525/54.31 X |
| 4,117,371 | 4/1980 | Holst et al. | 524/42 X |
| 4,133,784 | 4/1980 | Otey et al. | 524/52 X |
| 4,200,558 | 4/1980 | Holst et al. | 523/447 |
| 4,337,181 | 6/1982 | Otey et al. | 524/47 X |
| 4,454,268 | 6/1984 | Otey et al. | 524/47 |
| 4,560,372 | 12/1985 | Pieniak | 604/374 X |
| 4,676,784 | 6/1987 | Erdman et al. | 604/368 |
| 4,724,114 | 2/1988 | McFarland et al. . | |
| 4,826,880 | 5/1989 | Lesniak et al. . | |
| 4,985,467 | 1/1991 | Kelly et al. . | |
| 4,990,541 | 2/1991 | Nielsen et al. . | |
| 5,079,080 | 1/1992 | Schwarz | 428/288 |
| 5,087,513 | 2/1992 | Kim | 428/327 |

FOREIGN PATENT DOCUMENTS

| | | |
|---|---|---|
| 0157960 | 10/1985 | European Pat. Off. . |
| 255654 | 2/1988 | European Pat. Off. . |
| 0359615 | 3/1990 | European Pat. Off. . |
| 402650 | 12/1990 | European Pat. Off. . |
| 416405 | 3/1991 | European Pat. Off. . |
| 425269 | 5/1991 | European Pat. Off. . |
| 437816A1 | 7/1991 | European Pat. Off. . |
| 2392069 | 12/1978 | France . |
| 2930192 | 2/1980 | Germany ................ 264/5 |
| 57-92032 | 6/1982 | Japan . |
| 1034296 | 6/1966 | United Kingdom . |
| 2207369 | 2/1989 | United Kingdom . |
| 9011181 | 10/1990 | WIPO . |

OTHER PUBLICATIONS

"Superabsorbent Patents, Much More Than Just Diapers", B. J. Obenski; Nonwovens Industry, Nov. 1987, pp. 24–28.

"Non-Clammy Superabsorbent Material", Medical Textiles, vol. 5, No. 10, pp. 6–7, Elsevier Science Publishers, Ltd., England, 1989.

*Primary Examiner*—Thurman K. Page
*Assistant Examiner*—Peter F. Kulkosky
*Attorney, Agent, or Firm*—R. H. Hammer, III

[57] ABSTRACT

The present invention provides super absorbent materials in the form of sheets or fibers made from high melting polymers and having super absorbent polymer material dispersed uniformly throughout. The materials are capable of incorporating large amounts of super absorbent polymer and so demonstrate substantially improved absorbency and retention properties.

The superabsorbent materials comprise a matrix material polymer selected from the group consisting of cellulose esters, acrylic acid esters, polyvinyl esters and copolymers of same, particles of superabsorbent material distributed throughout the matrix material and a plasticizer mixed into the matrix material.

28 Claims, No Drawings

METHOD FOR IMMOBILIZING SUPERABSORBENT POLYMER AND PRODUCTS DERIVED THEREFROM

This is a continuation of application Ser. No. 07/805,538 filed Dec. 11, 1991, now abandoned.

FIELD OF THE INVENTION

This invention is directed to absorbent materials having superabsorbent polymer materials integrally incorporated therein. More specifically, it is directed to absorbent materials containing an immobilized uniform distribution of a superabsorbent polymer, and to methods of making them.

BACKGROUND OF THE INVENTION

Superabsorbent polymers (SAP) are synthetic cross-linked polymeric materials that are capable of absorbing many times their own weight in water and other liquids. Commercially, the materials are used as additives to increase the absorbency of such products as diapers, sanitary napkins, surgical dressings, disposable dust cloths, and the like (hereinafter "absorbent products").

The great commercial significance of these polymers is evidenced by the fact that over 5,000 patents have issued worldwide since 1966 directed to superabsorbent polymers and products. The majority of these have been for end use applications. Much of the current research and development continues to be to directed end use applications, including immobilizing the SAP in the absorbent product. See B. J. Obenski, "SUPERABSORBENT PATENTS, Much More than Just Diapers", *Nonwovens Industry*, pp 24–28, November 1987.

Because SAPs are significantly cross-linked, it is virtually impossible to put them into solution. Accordingly, SAPs are most commonly used as powders or granules. The use of SAPs in these physical forms presents product design problems as well as health risks. For example, the powdered material has a natural tendency to bunch up or agglomerate within the supporting matrix of the absorbent product. This results in uneven absorptive capacity in the product. Similarly, the fine particulates have a tendency to "dust-off" the supporting matrix resulting in loss of the SAP material altogether.

Powdered SAPs also pose health risks both to end users and those involved in the manufacturing process. The finely powdered SAP can become airborne where it can be inhaled by workers or end users. Once inhaled, the SAP absorbs liquid within the respiratory passages swelling to many times its original size. This can result in blocked air passages and potentially traumatic health complications.

A variety of methods have been suggested to resolve this problem. A conventional approach has been to simply disperse the powdered SAP material in a solid matrix material (e.g. wood pulp, cotton batting, etc.) and fix it in place mechanically as by embossing. That solution fails to completely eliminate bunching and adds costly processing steps.

An alternative to that approach, described in EP Patent Application 255,654, suggests the fabrication of dry formed sheets incorporating cellulose fibers and SAPs. The two materials are suspended in an air stream, fed to a head for dry-forming sheets of paper, laid down on a web, and bound by calendaring and embossing.

To eliminate added processing steps, U.S. Pat. No. 4,826,880 suggests forming hydrates of the SAPs. Such hydrates have reduced tendency to dust off a product and can be used in routine coating processes to coat conventional substrates such as cloth, nonwovens of various fibers, and vinyl films. These hydrates have reduced absorptive properties.

Other approaches effectively glue the particulate SAP material to a fibrous material, which is then mechanically immobilized in the substrate. PCT application WO 90/11811 discloses bicomponent fiber products in which fibers are coated with a liquid binder material. While the binder material is still wet, the particulate SAP is applied resulting in a comprehensive and uniform coating of the matrix fibers. The fibers are then fixed in a fabric or similar substrate by embossing or some such manner.

Still other approaches seek to affix the particulate SAP material to a matrix chemically. European Patent Application 402,650 discloses an absorbent mixture comprising both SAP particles and two phase particles made up of SAP bound to fiber pieces. The absorbent mixture is formed by mixing the monomeric SAP material in a liquid carrier, which is then dispersed within the fiber material, and polymerized and cross-linked "in-situ." Some of the SAP material becomes bound to the fibers. The resulting composite body is ground up to form the absorbent mixture. The absorbent mixture is then sandwiched between thin, nonwoven fibrous layers to form an absorbent article. The absorbent mixture tends to migrate throughout the absorbent article on the basis of particle size.

SAP materials have also been blended with thermoplastic materials for melt extrusion. For example, European Patent Application 425,269 discloses melt-spinnable fibers from thermoplastic materials containing SAP. Among the materials contemplated (but not shown to be suitable) for these fibers is cellulose acetate.

The principal drawback of such melt-spinning processes is that commercially significant superabsorbent polymer materials decompose when heated to temperatures above about 190° C. With decomposition, the SAP's absorbance capacity for aqueous liquids falls off precipitously and it becomes useless.

Cellulose acetate, even when combined with a plasticizer, must be heated to temperatures in excess of 230° to be processed by melt extrusion. Without plasticizer, higher temperatures are required. A number of other commercially significant materials also require temperatures in excess of about 200° C. to be processed by melt extrusion. Thus, it is not feasible to melt extrude SAPs with cellulose acetate or other high melting thermoplastics since the required temperatures are above the decomposition temperature of the superabsorbent polymers.

Additionally, because the superabsorbent polymer decomposes it can not be melted. Instead, when melt extruding SAP-containing materials, the SAP is mixed into the melt where it remains in solid, particulate form. There is an inherent limit to the amount of SAP that can be extruded in that fashion. EP 425,269 teaches that the upper limit of SAP in melt extrusion is 30% by weight. Beyond that point desired qualities of the product are lost.

There is a need for a safe, effective and economical method of immobilizing substantial quantities of superabsorbent polymers in a matrix material. Such a method would not result in thermal decomposition of the SAP and thus diminishment of its absorptive capacity. Further, the method would provide safe and effective absorptive products.

SUMMARY OF THE INVENTION

The present invention is directed to absorbent materials comprising a superabsorbent polymer immobilized in a hardened polymer matrix. The absorbent material is suitable for incorporation into absorbent products such as diapers, surgical dressings, etc. Because of the unique and surprisingly effective method of preparing these absorbent materials, they provide a variety of absorbent products that can absorb many times their original weight in aqueous liquid, are safe and are cost-effective to produce. A particularly surprising feature of these absorbent materials is that they are capable of absorbing greater than about 200 times their own weight of water.

The absorbent material of the present invention is fabricated by forming a liquid mixture of the matrix material and a suitable solvent. Such a liquid mixture is known generally within the art as a dope. Often the liquid mixture is a solution wherein the matrix material is completely solvated by a solvent.

The dope is supplemented with particulate or powdered superabsorbent polymer. Because of its substantially cross-linked character, the SAP is not solvated but remains as a suspension in the dope. The dope is extruded or cast to form sheets, films or fibers of matrix material having the SAP particulates embedded throughout. The resulting absorbent material is a matrix material within which is securely immobilized an SAP material that has retained substantially all of its original superabsorbency.

A particularly significant advantage of these solvent-based processes is the newfound opportunity to produce cost-effective securely immobilized SAP material at low temperature. Despite the great deal of attention and commercial interest, previous methods for immobilizing SAP have been only partially effective. Conventional methods have required costly processing steps that do not entirely eliminate migration of the SAP material within the absorbent product. Because of the known "dusting out" phenomenon, such approaches fail to eliminate health and safety risks.

Alternatively, some methods require high temperature processing conditions that drastically diminish the absorption capacity of the temperature sensitive SAP. Without low temperature processing, absorbency may be reduced or totally lost.

DETAILED DESCRIPTION OF THE INVENTION

The present invention provides absorbent products with very efficient immobilization of SAP that has substantial retention of absorbency. By substantial retention of absorbency is meant that the SAP has retained at least about 50% of its original liquid absorption capacity, i.e. the absorption capacity that the SAP had prior to incorporation into the matrix material. Frequently, retention of greater than 90% of original absorbency can be preserved. Under appropriate conditions, retention of nearly 100% original absorbency can be preserved. The present invention accomplishes this by providing methods for casting or extruding SAP-containing dopes at temperatures well below the thermal decomposition temperature of the SAP.

The superabsorbent polymers suitable for application in the present invention are conventional superabsorbent polymers as that term is commonly applied in the art. Examples of such materials are polymers of water soluble acrylic or vinyl monomers that are cross-linked with a polyfunctional reactant. Also included are starch modified polyacrylic acids and hydrolyzed polyacrylonitrile and their alkali metal salts. A more thorough recitation of SAPs is presented in U.S. Pat. No. 4,990,541, which is incorporated herein by reference.

A number of such SAPs are commercially available and these are also suitable for use in the present invention. A preferred commercially available superabsorbent polymer is Sanwet® a starch modified superabsorbent polymer available from Hoechst Celanese Corporation, Charlotte, N.C. Sanwet® is a starch grafted polyacrylate sodium salt that has the capacity to absorb as much as 800 times its own weight in liquid. Other commercially available SAPs are: DRYTECH® 520 SUPERABSORBENT POLYMER available from Dow Chemical Co., Midland, Mich. (Drytech® is a superabsorbent derived from polypropenoic acid.); AQUA KEEP manufactured by Seitetsu Kagaku Co., Ltd.; ARASORB manufactured by Arakawa Chemical (USA) Inc.; ARIDALL 1125 manufactured by Chemdall Corporation; and FAVOR manufactured by Stockhausen, Inc.

The preferred matrix materials of the present invention, when cast or extruded, harden into a non-expanded solid. By non-expanded solid is meant a compressed, or substantially continuous, hardened material. Thus, a non-expanded solid is a material that does not exhibit a visually discernable expanded structural network, e.g. the cellular structure of a foam. By a hardened, solid material is meant that it is not fluid. Despite being characterized as a hardened solid, these materials can be made to be very pliable and flexible. Similarly, the materials can be made to be porous as would be desirable for filtration membranes.

The matrix material of the present invention is also any hardenable polymeric material that can be solvated in a liquid carrier and solvent cast or extruded at temperatures below the decomposition temperature of the particular SAP utilized. Preferably, the matrix is one that after being cast or extruded hardens by the evaporation of the solvent into an amorphous solid. For purposes of this invention, hardened amorphous polymers are defined as any long chain polymer that does not, exhibit a uniformly distinct and definite crystalline structure in its solid, or hardened, state. Amorphous polymers are also referred to as non-crystallizing polymers and high-viscosity liquids.

Examples of suitable matrix materials include extruded or cast fibers or films of 1) cellulose esters and mixed esters (e.g., cellulose acetate [which term includes cellulose diacetate and triacetate], cellulose propionate, cellulose butyrate, and mixed esters thereof), 2) polymers of acrylic acid esters (e.g. polymethyl methacrylate and polyethyl methacrylate), and 3) polyvinyl esters (e.g. polyvinyl acetate). Suitable matrix materials further comprise copolymers and combinations thereof.

The matrix material may further comprise additives to enhance the physicochemical characteristics of the composition and the resulting product. Such additives include conventional plasticizers known to those skilled in the art. Examples of such plasticizers are phthalate esters (e.g., diethyl phthalate and dimethyl phthalate), phosphate esters, low molecular weight polymers (e.g., polypropylene glycol), oleates, sebacates, adipates, fatty acid esters, hydrocarbon derivatives, sulfonamides, and glycol derivatives (e.g., glycerin and modified glycerin such as triacetin).

It will be recognized by those skilled in the art that an advantage of the solvent-based processing systems is that they broaden the range of suitable matrix materials. For example, solvent-based extrusion of cellulose acetate can be very successfully performed using more inexpesive grades of polymer than those preferred for melt extrusion. Similarly, the use of additives commonly used in melt extrusion processes may be reduced or eliminated altogether. These and other advantages provide a more cost-effective product.

Another advantage is that the solvent-based extrusion process involves preparation of a suspension or mixture of solvated matrix material and superabsorbent polymer (collectively refered to as "solute"). These suspensions are capable of including significantly greater quantities of superabsorbent polymer than polymer melts used in melt extrusion methods. Such suspensions can contain greater than about 40% by weight solute (matrix material, additives, and SAP) of SAP. Preferably, the amount of SAP will be about 50% or greater of solute concentration. Most preferrably, the SAP concentration will be 70% of the solute concentration or greater.

Yet another advantage is the applicability of a wider range of grades of superabsorbent polymer. Melt extrusion of a dope containing superabsorbent polymers requires finely ground SAP. For example, EP application 425,269, supra., describes melt extrusion of SAP-containing melts wherein the SAP must be ground to particle sizes of 50 microns or less. The compositions of the present invention, however, can very satisfactorily use SAPs ground to particle sizes of up to about 450 microns. This too adds to the cost-effectiveness of the present compositions.

Thus, the present invention provides an absorbent material comprising a non-expanded, hardened matrix material and particles of a superabsorbent polymer distributed throughout the matrix material. In particular, the present invention provides very effective absorbent materials made with matrix materials having a melting temperature above the decomposition temperature of the superabsorbent polymer.

Additionally, the present invention provides an absorbent material comprising a non-expanded, hardened matrix material, and particles of a superabsorbent polymer distributed throughout the matrix material and constituting greater than about 40% by weight solids of the absorbent material.

The term "distributed throughout said matrix material" is intended to mean that the SAP is integrally incorporated into the physical structure of the matrix material itself. Thus, it is to varying degrees embedded within the matrix material and not merely superficially adhered to its exterior with a separate bonding agent.

The present invention also provides a composition comprising a stable suspension of a matrix material solvated in a solvent and particles of a superabsorbent polymer wherein said matrix material is selected from the group consisting of cellulose esters and mixed esters, polyvinyl acetate, and polyethyl methacrylate. By "stable suspension" is meant a mixture containing a substantially uniform distribution of solute and particulate material throughout a liquid carrier.

The present invention also provides a process for making an absorbent material comprising the steps of: providing a matrix material; solvating the matrix material in a suitable solvent; mixing particles of a superabsorbent polymer into said solvated matrix material to form a stable suspension; maintaining the temperature of the resulting suspension at less than the decomposition temperature of the superabsorbent polymer material; cooling the stable suspension; and desolvating the stable suspension or mixture. In the case where the process incorporates Sanwet ® as the superabsorbent polymer, the temperature of the suspension should be maintained at less than about 110° C. and preferably less than about 95° C.

Optimally, the cooling step comprises cooling the mixture to about −75° C. or lower for six hours or more.

Liquid carriers suitable for these applications are any nonaqueous solvent capable of creating an extrudable dope. Preferrably, the carrier will be chosen such that it is capable of completely solubilizing the matrix material in a concentration range that is acceptable for extruding the resulting dope. Such liquid carriers are known and recognized within the art. Examples of such liquid carriers include volatile, nonaqueous liquids such as low molecular weight aldehydes and ketones, hydrocarbons and halogenated hydrocarbons, esters and ethers. Examples of liquid carriers expressly capable of solubilizing cellulose esters are disclosed in U.S. Pat. No. 2,362,182, incorporated herein by reference. Those carriers include: acetone, methyl ethyl ketone, methyl acetate, ethyl acetate, propyl acetate, methyl formate, ethyl formate, propyl formate, and combinations thereof. Other suitable solvents are acetic acid, methylene chloride, methanol, and combinations thereof. Especially preferred solvents are acetone, methylene chloride, methanol, and combinations thereof.

Before extruding, the dope formed of the matrix material, liquid carrier and superabsorbent polymer is thoroughly mixed in a high shear mixing apparatus, e.g. a Jaygo 2 gallon pressure vessel with twin turbine, high shear mixer, model #3HP Lab Mixer. Preferably, the dope is mixed together by high shear mixing for about two hours or more. During this high shear mixing step the dope should be maintained at temperatures well below the decomposition temperature of the SAP. Preferrably, the temperature will be kept below about 125° C. After stirring, cooling should be applied. The mixture will preferrably be cooled to temperatures below 0° C. By keeping the temperature of the mixture below the decomposition temperature of the superabsorbent polymer, the superabsorbent polymer will retain nearly 100% of its original absorption/retention capacity.

To obtain maximum absorbancy, the mixture should be cooled for several hours. Optimum absorbancy of the resulting product has been observed by cooling the stirred mixture to about −78° C. or lower for six hours or more.

After the cooling step, the mixture is ready to be extruded or cast. During extrusion, the temperature of the dope may return to room temperature or even higher, however, the dope has a limited shelf-life at ambient temperatures and within a matter of hours the SAP will begin to drop out of suspension.

The resulting extruded or cast mixture can be desolvated in any conventional manner suitable for these processes known within the art. The selection of the particular drying method will depend on the matrix material, the solvent, and the end use for which the product is intended. For example, the product can be desolvated by heat, reduced pressure, or a combination of the two. The product can also be desolvated under ambient conditions.

The absorbent materials of the present invention can be extruded or cast into films, sheets, fibers, and variations thereof such as laminates and fibrils. The resulting compositions can readily be fabricated into consumer products such as diapers, surgical dressings and the like. Additionally, the absorbent materials may be fabricated into any end use requiring a material capable of absorbing considerable quantities of an aqueous liquid.

The following examples further illustrate various embodiments of the present invention. They are presented solely for purposes of illustration and are not to be interpreted as limitations of the invention.

EXAMPLES

Example 1

Effect of SAP Concentration

Using a high shear, 2 gallon mixer, a filtered cellulose acetate/acetone dope was diluted from 27% to 12% CA by the addition of acetone. The CA was cellulose diacetate commercially avilable from Hoechst Celanese Corp. product number HB 105. Three different compositions were prepared by adding to the dope Sanwet ® IM 1000 to constitute: a) 25%, b) 33%, and c) 50% solute concentration. All percents expressed herein are percent by weight, unless stated otherwise.

In each case, the addition of Sanwet ® was followed by high shear mixing for two hours. The mixture was then drained into half gallon containers and placed in a cooler containing dry ice overnight. The mixture was cold cast to a form a film by means of a film caster. The films were air dried and submitted for absorbency and retention testing. Table 1 (below) shows that absorbency increased with increasing percentage of Sanwet ®.

TABLE 1

Effects of % Sanwet on Absorbency/Retention

| | 0.9% Saline | | Deionized Water | |
|---|---|---|---|---|
| | Absorbency (g/g) | Retention (g/g) | Absorbency (g/g) | Retention (g/g) |
| 25% Sanwet | 9.4 | 7.2 | 49.4 | 37.0 |
| 33% Sanwet | 10.7 | 8.2 | 58.8 | 42.5 |
| 50% Sanwet | 16.3 | 11.3 | 84.8 | 62.3 |

Example 2

Temperature Effects

Using a high shear 2 gallon mixer, a filtered cellulose diacetate (HB 105)/acetone dope was diluted from 27% to 12% CA by the addition of acetone. Enough Sanwet ® IM 1000 was then added to constitute 50% of the percent solids concentration. The temperature adjustor connected to the mixer was then set to the desired temperature, −78° C., −10° C., 50° C., and 95.1° C. respectively for each trial period. At this temperature setting, mixing took place for two hours. The mixture was then drained in ½ gallon jars and cast to a film. The films were air dried and absorbency/retention tests were performed. Table 2 shows that colder storage temperatures enhanced absorbency and retention.

TABLE 2

Temperature Effects on Absorbency/Retention

| | 0.9% Saline | | Deionized Water | |
|---|---|---|---|---|
| | Absorbency (g/g) | Retention (g/g) | Absorbency (g/g) | Retention (g/g) |
| −78 deg. CA/Sanwet | 16.3 | 11.3 | 84.8 | 62.3 |
| −10 deg. CA/Sanwet | 10.6 | 7.4 | 59.9 | 44.0 |
| 50 deg. CA/Sanwet | 9.6 | | | |
| 95.1 deg. CA/Sanwet | 9.4 | 18.4 | 52.1 | 39.4 |

These have a 1:1 blend ratio

Example 3

Effect of Different Matrix Materials

The desired resin was dissolved in a suitable solvent (see below) to a 12% concentration. Sanwet ® IM 1000 was then added in an amount sufficient to constitute 50% of the solute concentration. Mixing took place in a high shear 2 gallon mixer for two hours.

The mixture was drained in ½ gallon containers and placed in a cooler containing dry ice overnight. The mixture was then cold cast to a film by means of a film caster. The limited results indicate that the cellulose esters performed best under cold temperature conditions. See Tables 3A–3D.

TABLE 3A

Blood Absorption and Retention Data

| Cryogenically Prepared Samples | Ovine Blood | | Bovine Blood | |
|---|---|---|---|---|
| | Absorbency (g/g) | Retention (g/g) | Absorbency (g/g) | Retention (g/g) |
| CTA/Sanwet | 9.2 | 8.0 | 8.8 | 7.2 |
| 25% Sanwet | 5.7 | 5.2 | 5.9 | 5.5 |
| 33% Sanwet | 6.7 | 5.3 | 7.1 | 6.0 |
| 50% Sanwet | 12.0 | 9.3 | 12.1 | 8.7 |
| CA/Sanwet/DEP | 14.7 | 12.0 | 15.6 | 11.5 |

Unless Specified 1:1 CA/Sanwet ratios exist
DEP = diethylphalate
CA = Cellulose diacetate, HB 105 (Hoechst Celanese Corp.)
CTA = Cellulose triacetate, RB 95 (Hoechst Celanese Corp.)
All matrix materials solvated in acetone except CTA
CTA solvated in $CH_2Cl_2$:$CH_3OH$ 91:9

TABLE 3B

Blood Absorption and Retention Data

| Noncryogenic Samples | Ovine Blood | | Bovine Blood | |
|---|---|---|---|---|
| | Absorbency (g/g) | Retention (g/g) | Absorbency (g/g) | Retention (g/g) |
| −10 deg. CA/Sanwet | 9.4 | 8.3 | 9.7 | 9.4 |
| 95.1 deg. CA/Sanwet | 7.8 | 7.1 | 9.0 | 7.2 |
| CA/18% DEP/Sanwet | 18.3 | 13.8 | 17.4 | 11.9 |

Unless Specified 1:1 CA/Sanwet ratios exist
DEP represents diethylphalate
CA = Cellulose diacetate, HB 105 (Hoechst Celanese Corp.)
CTA = Cellulose triacetate, RB 95 (Hoechst Celanese Corp.)

TABLE 3C

Effects of Polymers upon Absorbency/Retention

| Cryogenic 1:1 Blend Samples | 0.9% Saline | | Deionized Water | |
|---|---|---|---|---|
| | Absorbency (g/g) | Retention (g/g) | Absorbency (g/g) | Retention (g/g) |
| CA/Sanwet | 16.3 | 11.3 | 84.8 | 62.3 |
| CTA/Sanwet | 19.9 | 16.2 | 104.7 | 88.8 |
| CA*/Sanwet | 22.2 | | | |

TABLE 3C-continued

Effects of Polymers upon Absorbency/Retention

| Cryogenic 1:1 Blend Samples | 0.9% Saline Absorbency (g/g) | Retention (g/g) | Deionized Water Absorbency (g/g) | Retention (g/g) |
|---|---|---|---|---|
| CA/DEP/Sanwet Starch/Sanwet Noncompatible | 24.8 | 16.6 | 204.1 | 168.0 |
| Polystyrene/Sanswet Noncompatible | | | | |
| Polypropylene/Sanwet Noncompatible | | | | |
| PEMA/Sanwet | 11.2 | 2.6 | 20.4 | 16.6 |
| P-700/Sanwet Noncompatible | | | | |
| PVAC/Sanwet | 4.9 | | | |

*Woodfluff was also added to the CA
DEP = Diethylphalate (18%)
CA = Cellulose diacetate, HB 105 (Hoechst Celanese Corp.)
CTA = Cellulose triacetate, RB 95 (Hoechst Celanese Corp.)
PEMA = polyethylmethacrylate
P-700 = Polycaprolactone
PVAC = Polyvinylacetate

TABLE 3D

Effects of Polymers on Absorbency/Retention

| NonCryogenic 1:1 Blend Samples | 0.9% Saline Absorbency (g/g) | Retention (g/g) | Deionized Water Absorbency (g/g) | Retention (g/g) |
|---|---|---|---|---|
| PVAC/Sanwet | 4.5 | 2.8 | 37.1 | 28.8 |
| PEMA/Sanwet | 4.7 | 3.0 | 20.0 | 15.4 |
| CA/DEP/Sanwet | 22.6 | 16.8 | 188.0 | 159.4 |
| CA/Woodfluff/Sanwet | 12.2 | | | |

PVAC = Polyvinylacetate
PEMA = Polyethylmethacrylate
DEP = Diethylphalate
CA = Cellulose diacetate, HB 105 (Hoechst Celanese Corp.)

Example 4

Solvent Effects

Sanwet® was immobilized in cellulose diacetate (HB 105) in a variety of solvents. Dopes were prepared in accordance with the conditions of Example 1 except acetone was substituted with ethyl acetate, methylene chloride and acetic acid. The various solvents capable of solvating the cellulose acetate had no affect on absorbancy.

Example 5

Plasticizer Effects

Using a high shear 2 gallon mixer, filtered cellulose diacetate (HB 105) was diluted from 27% to 12% by the addition of acetone. Sanwet® IM 1000 was added to constitute 50% of the solids concentration. Diethyl phthalate (DEP) plasticizer was added to the mixture to 18% to enhance the film physicals. The mixture was stirred at high shear for two hours. The stirred mixture was drained into ½ gallon containers and placed in a cooler containing dry ice overnight. The mixture was then cast to a film both at room temperature and at reduced temperatures. Absorbency/retention improved both in films cast at room temperature and in cold cast films. See Tables 3.

Example 6

Analytical Test Method Determination of Total Absorbency and Centrifuge Retention The analytical procedure whereby absorbency and retention are measured follows.

Summary: The superabsorptive material ("SAM") is weighed dry and placed in a nylon bag. The nylon bag is placed in the fluid to be absorbed and weight gain is a measure of the absorptive capacity. The nylon bag is then placed in a special basket and centrifuged for a specified period of time (see below) to determine the amount of fluid retained.

Reagents Required: Saline solution ($0.900 \pm 0.005$ wt/wt % aqueous NaCl solution) or Citrated (anti-coagulant) certified disease-free animal blood.

Equipment and Materials Required:
1. Balance, accurate to the nearest 0.001 g.
2. Weighing boats or weighing paper.
3. 200 mesh nylon heat-sealable cloth stock or equivalent.
4. Timer, 30 minute minimum capacity.
5. Plastic pan, approximately 15"×20"×5" deep to hold test fluid.
6. Drying rack or line with clips.
7. Heat Sealer, Vertrod Model 9A, 9A-CAB or equivalent.
8. Deluxe Dynac II Centrifuge (Fisher Catalog No. 05-100-26) or equivalent.
9. Centrifuge retention basket.

Total Absorptive Capacity Procedure:
1. Cut Nylon cloth into 6×12 cm strips and seal two of the three open sides so the inside edges of the seals are about 3–5 mm from the edge of the bag. Predetermine the setting required on the sealer.
2. Accurately weigh 0.200 g ($W_1$) of SAM and place into the nylon bag and seal the bag.
3. Prepare five nylon bags containing SAM and two blanks (empty nylon bag) for each sample of SAM. Note: Before taking sample, slowly rotate the container end over end to mix. Be sure to take out a sample representing the entire particle size distribution when weighing. If it takes longer than 5 minutes to weigh and seal the bags and start the test, place the nylon bags in a desiccator.
4. Fill plastic container with 0.9% saline or blood to 1.5 inches in depth.
5. Hold the nylon bag containing the SAM horizontally and distribute the SAM throughout the nylon bag.
6. Lay nylon bag on the surface of the saline. Allow nylon bag to wet out for one minute before submerging.
7. After a soaking period of 60 minutes, remove bag.
8. Hang on line to drip for 15 minutes.
9. After 15 minutes drip time, weigh the blanks ($W_2$) and each bag containing SAM ($W_3$) and record weights.
10. Calculation:

Total Absorbency (g/g) =

-continued $$\frac{[\text{Wet Weight}(W_3) - \text{Blank Weight}(W_2)] - [\text{Net Dry Wt.}(W_1)]}{\text{Net Dry Wt.}(W_1)}$$

Take the average of the 5 nylon bags and report as total absorbency in g/g.

Centrifuge Retention Procedure:
1. Place paper towels around the bottom and insides of the centrifuge in order to absorb the fluid that is removed. Place the towels carefully so that they do not touch the basket.
2. Place two bags from the total absorbency and the two blanks in the centrifuge basket. Position the bags so that the blanks are opposite each other and the bags containing the samples are opposite each other for proper balancing.

Note: Place the nylon bags containing the sample in the centrifuge such that the bags do not overlap the top of the basket with the folded ends down. As many as six-10 bags may be centrifuges at one time.
3. Close the centrifuge lid.
4. Start the centrifuge and ramp up quickly to 1600 RPM. Once the speed is stable at stable at 1600 RPM, set the timer for three minutes.
5. After three minutes at 1600 RPM, turn off the centrifuge and apply the brake.
6. Remove the bags and weigh each and record the weights. Use the average of the two blank weights ($W_4$) and the average of the two sample bag weights ($W_5$) for the calculation.

$$\frac{[\text{Wet Weight}(W_5) - \text{Blank Weight}(W_4)] - [\text{Net Dry Wt.}(W_1)]}{\text{Net Dry Wt.}(W_1)}$$

Report centrifuge retention in g/g.

What is claimed is:

1. An absorbent material comprising a solution spinnable or solution extrudable matrix material, said matrix material being selected from the group consisting of cellulose esters, acrylic acid esters, polyvinyl esters, and copolymers and combinations of the foregoing, particles of a superabsorbent polymer distributed throughout the matrix material, and a plasticizer mixed into said matrix material, said plasticizer being present in an amount sufficient to enhance said absorbent materials's absorbency and retention properties, said plasticizer being selected from the group consisting of phthalate esters, phosphate esters, low molecular weight polypropylene glycol, oleates, sebacates, adipates, fatty acid esters, hydrocarbon derivatives sulfonamides, and glycol derivatives.

2. A molded or shaped article formed of the absorbent material of claim 1.

3. The absorbent material of claim 1 wherein said plasticizer being selected from the group consisting of phthalate esters, phosphate esters, and glycol derivatives.

4. The absorbent material of claim 1 wherein the plasticizer is a phthalate ester.

5. The absorbent material of claim 1 wherein the plasticizer is diethyl phthalate.

6. The absorbent material of claim 5 wherein diethyl phthalate comprises about 18% by weight solids.

7. The absorbent material of claim 1 wherein the matrix material is a cellulose ester selected from the group consisting of cellulose acetate, cellulose propionate, cellulose butyrate, and mixed esters thereof.

8. The absorbent material of claim 1 wherein the superabsorbent polymer constitutes at least about 40% by weight of the material.

9. The absorbent material of claim 1 wherein the superabsorbent polymer constitutes at least about 60% by weight of the material.

10. The absorbent material of claim 1 wherein the superabsorbent polymer is a sodium salt of a grafted starch polyacrylate.

11. An absorbent material comprising a solution spinnable or solution extrudable matrix material, said matrix material being selected from the group consisting of cellulose esters, acrylic acid esters, polyvinyl esters, and copolymers and combinations of the foregoing, particles of a superabsorbent polymer distributed throughout the matrix material and constituting greater than about 40% by weight solids of the absorbent material, and a plasticizer mixed into said matrix material, said plasticizer being present in an amount sufficient to enhance said absorbent material's absorbency and retention properties, said plasticizer being selected from the group consisting of phthalate esters, phosphate esters, low molecular weight polypropylene glycol, oleates, sebacates, adipates, fatty acid esters, hydrocarbon derivatives, sulfonamides, and glycol derivatives.

12. A molded or shaped article formed of the absorbent material of claim 11.

13. The absorbent material of claim 11 wherein the matrix material is selected from the group consisting of cellulose acetate, cellulose propionate, cellulose butyrate, mixed esters thereof, polyvinyl acetate and polyethyl methacrylate.

14. The absorbent material of claim 11 wherein said plasticizer being selected from the group consisting of phthalate esters, phosphate esters, and glycol derivatives.

15. The absorbent material of claim 14 wherein the plasticizer is a phthalate ester.

16. The absorbent material of claim 14 wherein the plasticizer is diethyl phthalate.

17. The absorbent material of claim 16 wherein diethyl phthalate comprises about 18% by weight solids.

18. A composition comprising a stable suspension of a cellulose ester or a mixture of cellulose esters matrix material, particles of a superabsorbent polymer, and a plasticizer mixed into said matrix material, said plasticizer being present in an amount sufficient to enhance said absorbent material's absorbency and retention properties, said plasticizer being selected from the group consisting of phthalate esters, phosphate esters, low molecular weight polypropylene glycol, oleates, sebacates, adipates, fatty acid esters, hydrocarbon derivatives, sulfonamides, and glycol derivatives in a liquid carrier.

19. The composition of claim 18 wherein the cellulose ester matrix material is selected from the group consisting of cellulose acetate, cellulose propionate, cellulose butyrate, and mixed esters thereof.

20. A composition comprising a stable suspension of a matrix material, particles of a superabsorbent polymer and a plasticizer in a liquid carrier, the matrix material being selected from the group consisting of polyvinyl esters and polymers of acrylic acid esters, and the liquid carrier being selected from the group consisting of acetone, methanol, methylene chloride, and combinations thereof, and the plasticizer mixed into said matrix material, said plasticizer being present in an amount sufficient to enhance said absorbent material's absorbency and retention properties, said plasticizer being selected from the group consisting of phthalate esters, phosphate esters, low molecular weight polypropylene glycol, oleates, sebacates, adipates, fatty acid esters, hydrocarbon derivatives, sulfonamides, and glycol derivatives.

21. A process for making an absorbent material containing a superabsorbent polymer comprising of steps of:
    solvating a matrix material in a suitable solvent, the matrix material being selected from the group consisting of cellulose esters, acrylic acid esters, polyvinyl esters, and copolymers and combination of the foregoing;
    mixing particles of a superabsorbent polymer and a plasticizer into said solvated matrix material to form a stable suspension and said plasticizer mixed into said matrix material, said plasticizer being present in an amount sufficient to enhance said absorbent material's absorbency and retention properties, said plasticizer being selected from the group consisting of phthalate esters, phosphate esters, low molecular weight polypropylene glycol, oleates, sebacates, adipates, fatty acid esters, hydrocarbon derivatives, sulfonamides, and glycol derivatives;
    cooling the stable suspension; and
    desolvating the stable suspension.

22. The process of claim 21 wherein the stable suspension is formed by mixing the composition at high shear for at least about two hours.

23. A process for making an absorbent material containing a superabsorbent polymer comprising the steps of:
    solvating a matrix material in a suitable solvent, the matrix material being selected from the group consisting of cellulose esters acrylic acid esters, polyvinyl esters, and copolymers and combination of the foregoing;
    mixing particles of a superabsorbent polymer and a plasticizer, said plasticizer mixed into said matrix material, said plasticizer being present in an amount sufficient to enhance said absorbent material's absorbency and retention properties, said plasticizer being selected from the group consisting of phthalate esters, phosphate esters, low molecular weight polypropylene glycol, oleates, sebacates, adipates, fatty acid esters, hydrocarbons derivatives, sulfonamides, and glycol derivatives into said solvated matrix material;
    forming a stable suspension of said matrix material, solvent an superabsorbent polymer by high shear stirring at temperatures less than about 95° C. for about two hours;
    cooling the suspension to about −78° C. for at least about 6 hours; and
    desolvating the suspension.

24. The process of claim 23 wherein said plasticizer being selected from the group consisting of phthalate esters, phosphate esters, and glycol derivatives.

25. The process of claim 23 wherein the plasticizer is diethyl phthalate.

26. The process of claim 24 wherein the diethyl phthalate is added in sufficient quantity to comprise about 18% by weight solute.

27. The process of claim 22 wherein the cellulose ester is selected from the group consisting of cellulose acetate, celoulose propionate, cellulose butyrate, and mixed esters thereof.

28. The process of claim 22 wherein the suitable solvent is selected from the group consisting of acetone, methyl ethyl ketone, methyl acetate, ethyl acetate, propyl acetate, methyl formate, ethyl formate, propyl formate, methylene chloride, methanol, and combinations thereof.

* * * * *